United States Patent
LaBudde et al.

(10) Patent No.: US 6,607,524 B1
(45) Date of Patent: Aug. 19, 2003

(54) SURGICAL LASER AND METHOD OF ABLATING HARD BIOLOGICAL MATERIALS

(75) Inventors: Edward V. LaBudde, Westlake Village, CA (US); Robert A. LaBudde, Virginia Beach, VA (US)

(73) Assignee: Pharos Optics, Inc., Los Angeles, CA (US)

(*) Notice: Subject to any disclaimer, the term of this patent is extended or adjusted under 35 U.S.C. 154(b) by 0 days.

(21) Appl. No.: 09/512,391

(22) Filed: Feb. 24, 2000

Related U.S. Application Data (63) Continuation-in-part of application No. 08/908,323, filed on Aug. 7, 1997, now abandoned.

(51) Int. Cl.$^7$ ............................................. A61B 18/18
(52) U.S. Cl. .............................. 606/10; 606/13; 606/15; 606/27; 604/20
(58) Field of Search ............................. 606/3, 10–16, 606/27; 604/20

(56) References Cited

U.S. PATENT DOCUMENTS

| | | |
|---|---|---|
| 3,503,804 A | 3/1970 | Schneider |
| 3,821,510 A | 6/1974 | Muncheryan |
| 4,002,877 A | 1/1977 | Banas |
| 4,066,138 A | 1/1978 | Salisbury |
| 4,987,286 A | 1/1991 | Allen |
| 5,020,995 A | 6/1991 | Levy |
| 5,092,864 A | 3/1992 | Hayes et al. |
| 5,199,870 A | 4/1993 | Steiner et al. |
| 5,246,436 A | 9/1993 | Rowe |
| 5,257,935 A | 11/1993 | Vassiliadis |
| 5,267,856 A | 12/1993 | Wolbarsht |
| 5,318,562 A | 6/1994 | Levy et al. |
| 5,324,200 A | 6/1994 | Vassiliadis |
| 5,342,198 A | 8/1994 | Vassiliadis |
| 5,401,171 A | 3/1995 | Paghdiwala |
| 5,609,284 A | 3/1997 | Kondratenko |

FOREIGN PATENT DOCUMENTS

| | | | |
|---|---|---|---|
| WO | WO9707928 | 3/1997 | ........... B23K/26/14 |

OTHER PUBLICATIONS

Altshuler, G. et al., "Physical Aspects of Cavity Formation of Er–Laser Radiation", 6/95, SPIE vol. 2394, p. 211–222.
Jacques, S. et al., "Laser–Tissue Interaction V", 1/24–27/94, SPIE vol. 2134A p. 309–317.

*Primary Examiner*—David M. Shay
(74) *Attorney, Agent, or Firm*—Koppel, Jacobs, Patrick & Heybl (57) ABSTRACT

A method and apparatus for use in ablating hard and soft tissue and in particular, tooth, tooth enamel, tooth dentin, tooth cementum, bone, cartilage, skin, mucosa, gingiva and muscle, and preferably in the oral cavity, is disclosed. In operation, an electromagnetic energy source is applied to a target material producing thermo-elastic failure resulting in fracture or rupture of the material. When this point is reached, the energy source is stopped and immediately a fracturing fluid is applied to the lasing site with sufficient cooling power, solvating power, and momentum to not only cause further fracture or rupture of the material but also to remove debris from the site. The process is repeated until the desired ablation is effected.

32 Claims, 11 Drawing Sheets

SURGICAL LASER AND METHOD OF ABLATING HARD BIOLOGICAL MATERIALS

This application is a continuation-in-part of application Ser. No. 08/908,323, filed Aug. 7, 1997 now abandoned, to which priority is claimed under 35 U.S.C. 120.

BACKGROUND OF THE INVENTION

1. Field of the Invention

The present invention relates to a device and method for cutting hard and soft tissue and in particular, teeth, tooth enamel, tooth dentin, tooth cementum, bone, cartilage, skin, mucosa, gingiva, and muscle, and preferably in the oral cavity.

2. Background of Related Art

The use of lasers for oral applications was reported as early as 1964. While such reports indicated that lasers could be used on dental hard tissue, lasers have not generally been used clinically until recently for surgical purposes, including drilling or cutting of teeth, primarily because of the large amount of damage caused to the material and its surrounding tissue by the laser. Such damage is generally caused by excessive heating of the surgical site and its surrounding material due to the amount of energy required by the laser to cut the material. However, recent developments with the use of pulsed eximer and infrared lasers on soft and hard tissue has shown promise, resulting in cutting of these materials with less damage then previous lasers.

Infrared Erbium lasers are suitable for cutting soft and hard biological tissue. This is because of the high absorption that biological tissues have for laser energy at the wavelength generated by these lasers, 2.7 $\mu$m to 2.94 $\mu$m. This high level of absorption is due largely to the high water content of these materials since water has an absorption coefficient of about 10,000 to 13,000 per centimeter at these wavelengths. As a result, many researchers have attempted to improve to the cutting ability of Erbium lasers by adding of externally applied high energy absorptive fluids, such as water, primarily for the purpose of cooling the material being cut and its surrounding tissue. The disclosure of the following patents are incorporated into this application by reference.

In Vassiliadis et al., U.S. Pat. Nos. 5,257,935, and 5,342,198, the application of water is disclosed, not for use as a cutting aid but for cooling the lazed material, if necessary. Both Vassiliadis patents teach the use of a laser to eradicate, by vaporization, tooth material by exposing the tooth to the laser radiation followed by a water spray if heating does occur. While the patent states that the apparatus obliterates dental enamel and dentin without significant heating, it is known that the heating of tooth material to facilitate obliteration must be conducted at ablation rates that are somewhat less then optimal or else unwanted charring and discoloration of the tooth material will occur. Additionally, vaporization of tooth material requires quite high temperatures which in turn promotes tissue and tooth damage.

U.S. Pat. No. 5,401,171, to Paghdiwala, discloses the use of a handheld tool containing a built in laser and delivery system which focuses the laser energy on a surface to be cut. Paghdiwala additionally discloses the use of externally applied water to cool the surface being cut, thereby preventing excessive heating.

Allen, U.S. Pat. No. 4,987,286, discloses the use of water illuminated by laser light to remove particles adhered to a surface without the danger of damaging the underlying surface. In Allen, the process removes particles and contaminates adhered to the surface of a base material by laser energy which excites a fluid, typically water, surrounding the particles. The laser causes the water to explosively evaporate with sufficient force to remove the attached particles, but without cutting into or causing damage to the base surface material.

Steiner et al., U.S. Pat. No. 5,199,870 teaches the use of a thin layer of absorbing fluid, on the order of 10 to 200 microns, applied to the surface of the tooth prior to the application of laser light. They claim that Laser light heats the liquid, causing the liquid to expand and cool the tissue surrounding the cutting location.

Wolbarsht et al., U.S. Pat. No. 5,267,856 teaches the use of a fluid which is applied to a material prior to or during a laser pulse, permitting the fluid to enter into pores and cracks of the material, instead of remaining pooled on the surface. The invention requires that the water, or whatever liquid or radiation absorbent substance used, must infiltrate into the pores of the material without forming a barrier to penetration of the laser radiation into the material surface. The pooled fluid can be removed by moist air before the laser light is applied; dry air should not be used to blow of the excess water unless care is taken to be sure water remains in the pores. The ablation of the material by this process results from the expansion of the fluid seeped into the pores. However, since many materials such as tooth enamel are not very porous, and since other human hard tissue already has high levels of internal water present in the tissue, the penetration rate of such liquids into living tissue is very low, limiting the effectiveness of this cutting method.

Biolase Technology, Inc. PCT Patent Application No. PCT/US96/13960 teaches a process in which a mist of atomized particles is introduced into a volume of air above a target surface to be cut. A laser is focused into the mist causing the atomized particles to explode and impart mechanical cutting forces to the target surface. Accordingly, the exploding fluid particles rather then the direct laser energy source cuts the tissue; the laser energy itself is not directly absorbed by the target material. While this method may provide some level of ablation of the target material, it is not very efficient because (1) the water absorbs the laser energy and the heat of vaporization which is lost and can not be converted into cutting energy, and (2) the particles accelerated by the explosion of the water bounce off the target tissue due to the high acoustic impedance of the target surface, imparting little energy to the target material.

The use of an absorbing fluid in Steiner and Wolbarsht et al. has inherent efficiency limitations. Ideally, one would want a synergistic effect to be generated by the laser in directly ablating a surface material and interacting with the applied fluid to further enhance the ablation process. However, with the above processes this is not possible because the fluid has a great affinity for the laser energy causing the laser to first interact with the fluid and convert it to a gas. All the energy used to heat the fluid to a gas (latent heat of vaporization) is lost and not available for the ablation process. This conversion takes place during the initial portion of the laser pulse, and prior to actual ablation of the material surface. The fluid is thus blown away by gaseous expansion prior to the ablation and is therefore is not available during the remainder of the laser pulse. In addition, the use of a fluid alone, such as water, is insufficient in many materials to generate ablation forces since the force produced by the fluid gasification pressure is not high enough to fracture the material. Thus, the use of an absorbing fluid may actually lower the efficiency of the cutting system, resulting in inefficient use of the laser energy with less than optimum performance results.

The process of cutting by vaporization, as disclosed in Vassiliadis, also has inherent efficiency limitations. The cutting of tooth material by vaporization required quite high temperatures, typically on the order of 2,000 C. Thus cutting must be conduced quite slowly in order to prevent heating and damage to the tooth and surrounding tissue. If higher cutting rates are attempted, charring or burning of the tooth and surrounding tissue can occur as well as permanent damage to live tooth and tissue structure.

SUMMARY OF THE INVENTION

The present invention involves a device and method for ablating hard and soft tissue and, in particular, teeth, tooth enamel, tooth dentin, tooth cementum, bone, cartilage, skin, mucosa, gingiva, and muscle, and preferably in the oral cavity. This is accomplished by interacting an electromagnetic energy source, typically a laser, with a dry tissue surface to heat the surface to a temperature at which thermoelastic failure (thermal expansion induced stresses) of the material takes place due to rapid heating. This heating results in the "crumbling" or "snapping" of the tissue rather then vaporization. When this point is reached, the laser energy is stopped and a cool fluid is immediately applied to the ablation site to create additional thermal stresses, resulting in further ablation of tissue by the thermal expansion stress of rapid cooling. In addition, the fluid is delivered to the ablation site with sufficient momentum so that it not only quickly cools the site but also scrubs and flushes the surface of debris (because the process does not vaporize the material), flushing particles off of the surface and out of the lasers field of view. The momentum of the fluid flow is also high enough so that all or most of the fluid delivered to the ablation site bounces off, leaving the surface relatively free of the fluid and without the fluid seeping into the material's pores or cracks.

The present invention also addresses a method and apparatus for a laser delivery system which reduces the absorption of ablated debris. This is accomplished by directing the fluid so that it not only forcibly remove debris from the ablation site, but also interacts with the tip of the laser delivery source to keep it free of contaminates. The fluid utilized may be gaseous or liquid and is an efficient solvent for flushing the target material. The fluid is preferably non-absorbent of the lasing energy having heat capacity and latent heat of vaporization.

BRIEF DESCRIPTION OF THE DRAWINGS

These and other features, aspects and advantages of the present invention will be apparent to those skilled in the art from the following detailed description, together with the accompanying drawings in which.

DETAILED DESCRIPTION OF THE INVENTION

The present invention provides an apparatus and a method for cutting and/or drilling hard and soft tissue, preferably hard and soft tissue located in the mouth. A high intensity beam, preferably from an Erbium laser, is directed to an ablation site by an optical delivery system. The laser light is emitted from the delivery system and impinges upon the ablation site, heating the material until thermally induced failure is reached, at which point the lasing process is stopped and the ablation site is subjected to a fluid stream which cleans and rapidly cools the ablation cite with high efficiency causing further mechanical failure and also removes debris material. This process is repeated until the required amount of material has been removed.

Figure 1:
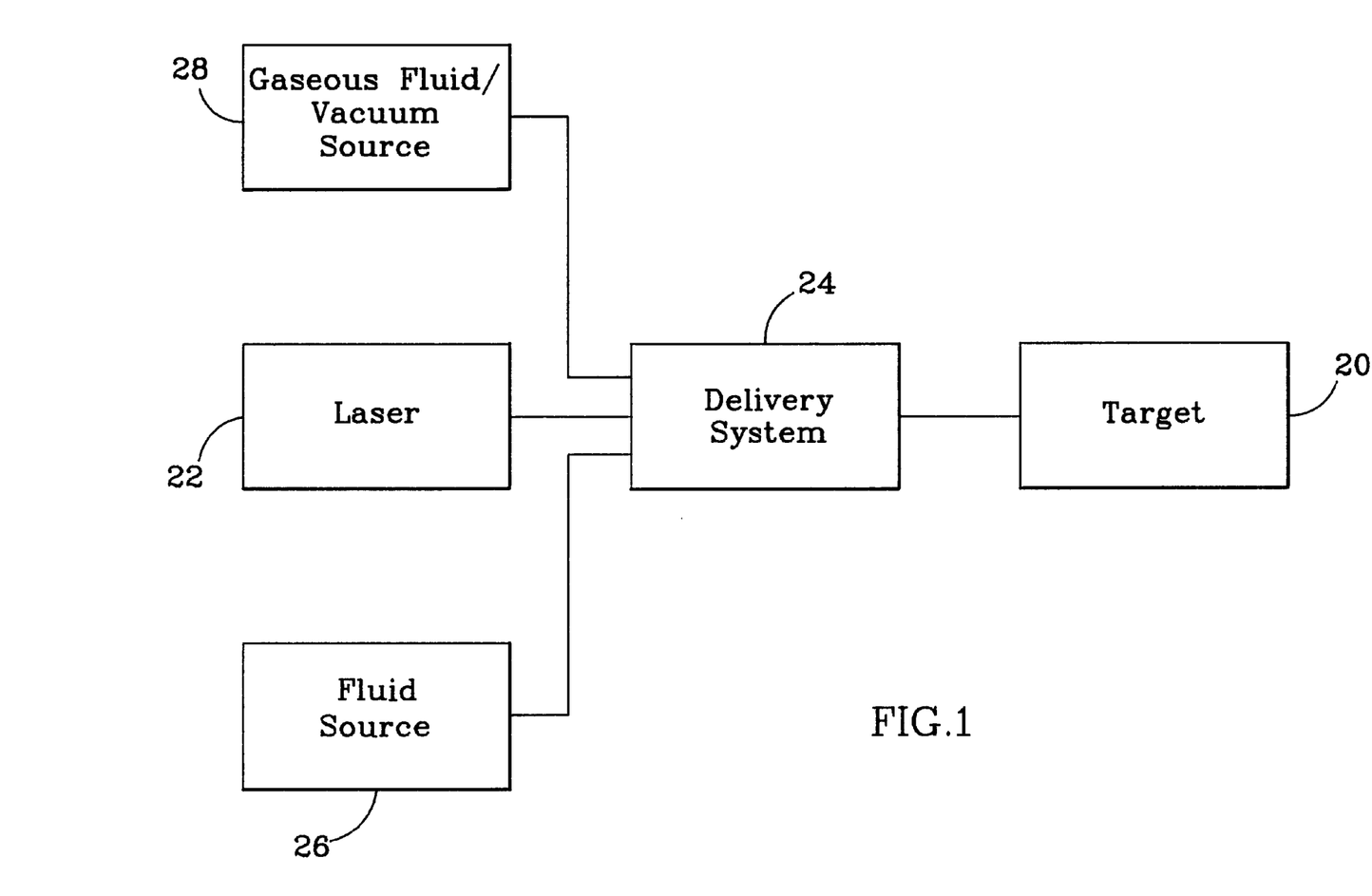
FIG. 1 is a is a block diagram of the present invention.

The invention, as depicted in FIG. 1, is used to cut and/or drill a target material 20, typically a tooth, tooth enamel, tooth dentin, tooth cementum, bone, cartilage, skin, mucosa, gingiva or muscle, and preferably in the mouth. It includes an electromagnetic generating energy source, commonly a laser 22, which transmits a beam to a delivery system 24. Also connected to delivery system 24 is a fracturing fluid source 26 and a gaseous fluid/vacuum system 28. Both systems 26 and 28 contain, among other things, fluid pumps or vacuums (not shown) as required. Delivery system 24 directs the laser beam, the fluid from fluid source 26 and gas or vacuum, as required, to target 20.

Figure 2:
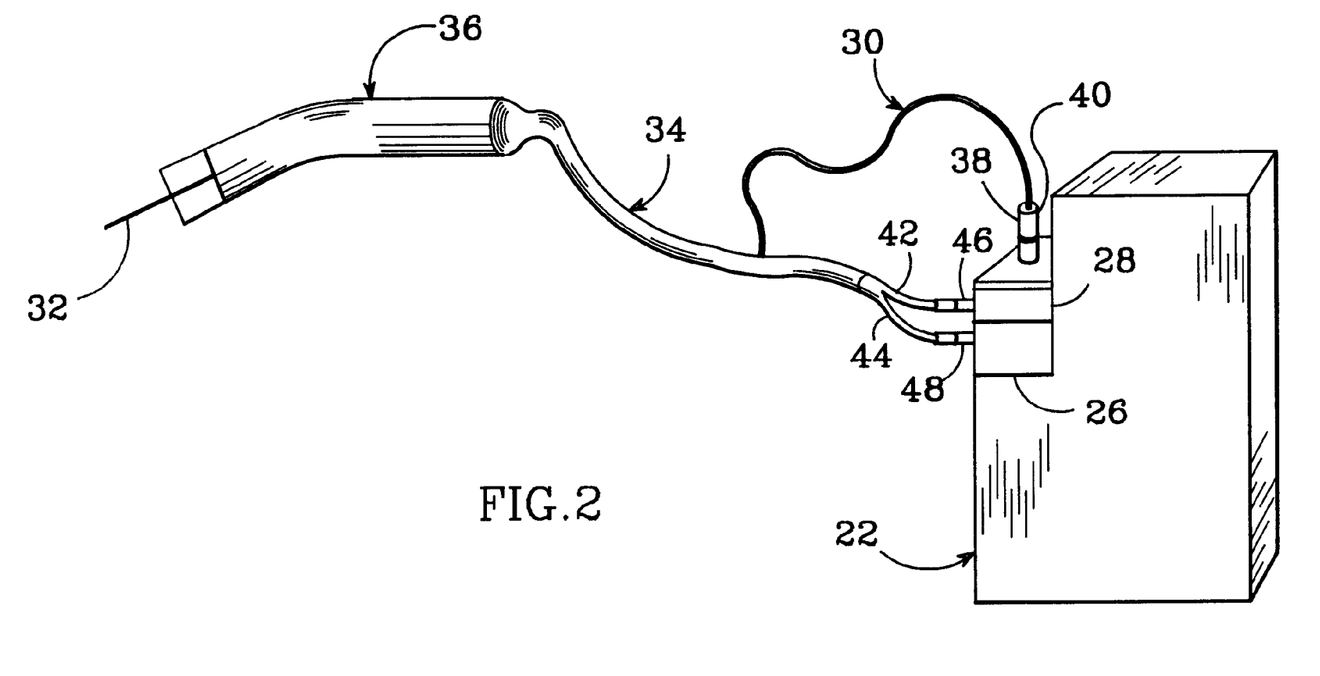
FIG. 2 is an elevation view of one embodiment of the invention.
Figure 3:
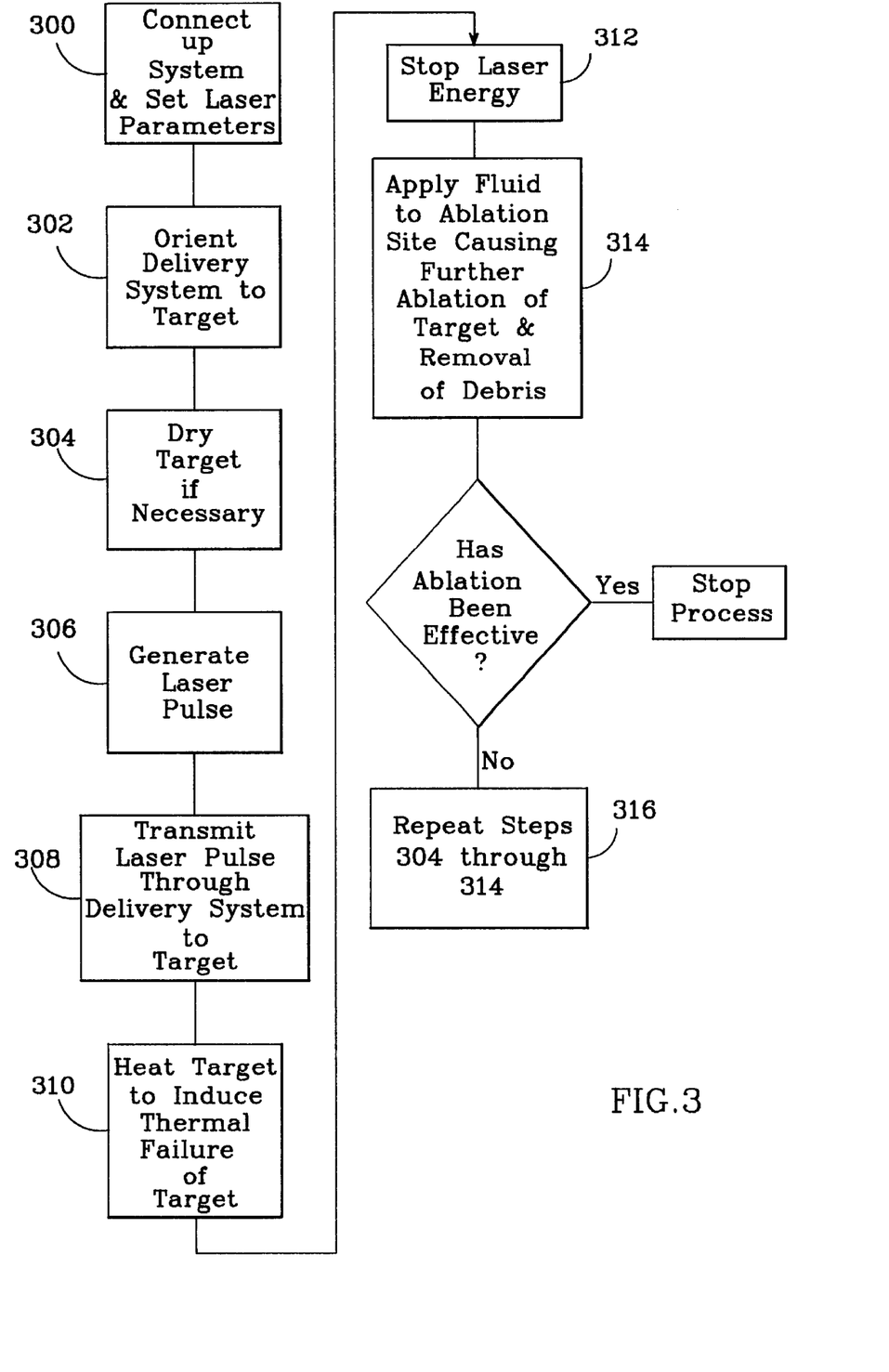
FIG. 3 is a flow chart depicting the method used by the invention to ablate material.

The system of the present invention, as depicted in FIGS. 2 and 3, consists of a laser 22 that delivers a beam of laser light to a target site 20 via a fiber optic cable 30. While a single cable 30 can be used it is often desirable to utilize a second fiber 32 interfacing at one end with fiber 30 and at its second end delivering the laser light to target 20. Fiber 30, is relatively long and is provided in a protective cabling (not shown). Both fiber 30 and its protective cabling are housed in a sheath 34. Fiber 30 has one end coupled to laser 22 and another end coupled to handpiece 36. A sub-miniature type-A (SMA) connection including an SMA connector 38 plugs into a port 40 coupling fiber 30 to laser 22. Gas/vacuum and fracturing fluid are supplied to hand piece 36 via a set of supply lines 42 and 44 respectively. Both lines 42 and 44 are housed within sheath 34 connected at one end to their respective source 28 and 26, by ports 46 and 48 and at a second end to handpiece 36.

Second fiber 32 is optically coupled to fiber 30 in handpiece 36. Preferably, fiber 32 is provided mounted in a ferrule (to be discussed in greater detail below) to form a disposable fiber optic tip, which can be easily removed from handpiece 32. Accordingly, in the event the tip of fiber 32 is damaged or contaminated, the fiber optic tip can be discarded and readily replaced with a new one.

In operation, lines 42, 44 and fiber 30, contained within sheath 34, are connected at a first end to their respective ports 46, 48, and 40, and at a second end to handpiece 36. After connection, laser 22, air vacuum source 28, and fluid source 26 are turned on and the laser parameters are set (step 300). Handpiece 36 is then positioned with respect to target 20 with fiber 30 or 32, as the case may be, located approximately 1 to 2 millimeters away from target 20 (step 302).

If target 20 appears to be wet, having a liquid coating of approximately 10 microns or more, the liquid should be first removed. The removal process enhances laser cutting efficiency in that if a liquid is present at the start of the lasing operation, the liquid must first be removed by the laser prior to laser energy being received by the target material. While the liquid on the tooth at the beginning of the pulse may aid in cooling the target area from excessive heating, it inhibits cutting of the ablation site. Target 20 can be dried by a variety of methods, for example by the use of dry air or vacuum, by a first short, or low power, laser pulse prior to the ablation pulse, by a water jet having sufficient momentum to not only remove the surface liquid but also carry both products away, or by conventional method known by those skilled in the art (step 304).

If the surface of target 20 is dry, or the quantity of liquid is negligible, laser 22 is activated generating a laser pulse in the form of a light beam (step 306) which is provided to delivery system 24 and ultimately to target 20 (step 308). It is preferred that the wavelength of light generated by laser 22 be between about 2 micrometers to about 3 micrometers or between about 9 micrometers to about 11 micrometers as these wavelengths are highly absorbed by human tissue. It is more preferred that the wavelength of the laser light be between about 2.7 micrometers and about 3.0 micrometers, with the most preferred wavelength being at 2.94 micrometers.

It is also desirable that laser 22 be capable of producing a pulsed energy output. The pulsed energy output is generally characterized by a combination of the pulse width, the duration of the laser pulse, the pulse shape, the energy distribution of the laser, and the repetition rate, the rate at which the laser pulse is delivered. The pulse width should be chosen so as to create the maximum ablation depth in the target 20. If the pulse width is too short, only a thin layer near the surface of target 20 is heated, limiting the ablation depth. If the pulse width is too long, the penetration depth is too deep and a reduction in thermal gradient limits ablation depth. At each wavelength, there is an optimum pulse width; for 3 micrometers the optimal pulse width is between 100 microseconds and 400 microseconds. As for the pulse shape, the pulse should be near uniform with a fairly rapid ramp-up permitting rapid heating of the target 20 and with a tapering ramp-down, keeping the ablation site hot. If liquid is found to be present on target 20, the pulse shape can be modified to concentrate more laser energy near the leading edge of the pulse so as to quickly bum of any residual liquid allowing greater time for heating the target 20. Lastly, one must consider the repetition rate. In the present invention, the laser light must be applied in a pulsed fashion so as to allow the alternating heating-cooling-flushing action to occur in rapid succession. The repetition rate should be as high as possible to permit rapid cutting, limited only by the time it takes to thermally fracture the target material and remove the absorbing debris. Repetition rates between 5–50 Hz are desirable.

Figure 4A:
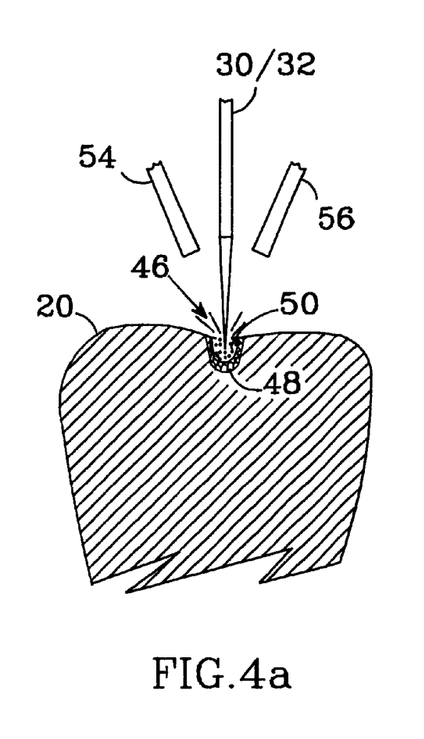
FIGS. 4(a)–4(c) are sectional views illustrating the progress of ablating a target material.

In operation, Laser 22, via delivery system 24, is used to heat target 20 at an ablation site 46 producing thermally-induced failure of the material (step 310). The temperature necessary to induce such failure in hard tissue (teeth, bone, dentin, enamel) is about 500 C., and less for soft tissue. At such temperatures, thermo-inducted failure of the target 20 will occur forming a crater 48 at ablation site 46 and debris 50 in the form of small particles of tissue will be formed, see FIG. 4(a). The threshold energy to accomplish such failure is about 7.5 $J/cm^2$ to about 15 $J/cm^2$. Quite often debris 50 is found to remain in crater 48 or sometimes adhered to the end of fiber 30/32, in both situations, debris 50 unnecessarily absorbs the laser energy lowering the system efficiency. However, it has been found that if a debris free environment can be achieved, laser power on the order of about 40 $J/cm^2$ to about 80 $J/cm^2$, or more, can be use to create thermally-induced failure of target 20, thus increasing cutting efficiency but yet without harmful effects to the target tissue.

Figure 4B:
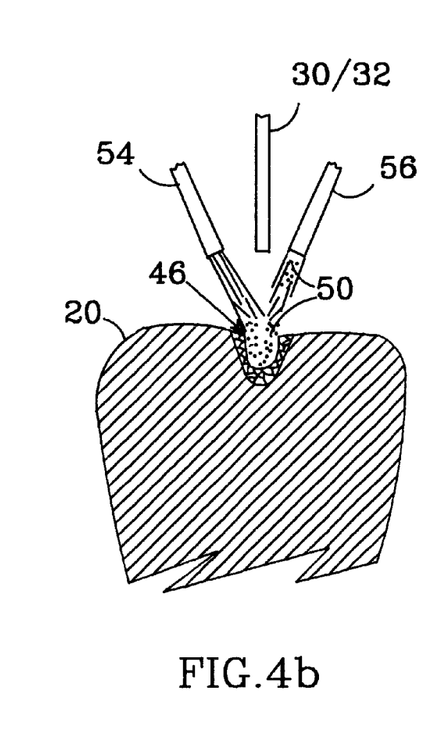

At the end of the laser pulse, laser 22 is stopped preventing further laser light from being generated (step 312). Immediately after stopping laser 22, a fracturing fluid 52 is delivered to ablation site 46 from fluid source 26 by one or more fluid jets 54 resulting in further ablation of target 20. It is theorized that this further ablation is a result of mechanical failure of the target material due to thermal induced stresses. Additionally, fracturing fluid 52 is delivered by fluid jet 54 with sufficient momentum to remove debris 50 from crater 48, see step 314 and FIG. 4(b). Preferably fluid 52 is applied at a rate of about 0.1 cc per second to about 1 cc per second and at velocities of about 50 meters per second or more. Ideally, fluid 52 would be selected such that it does not absorb the laser energy, so that in the event that any fluid 52 is present during the lasing operation it will not effect the systems efficiency, an example of such a fluid 52 is an alcohol such as ethanol. While fluid 52 can a singular fluid, mixtures of fluids are also contemplated.

Figure 4C:
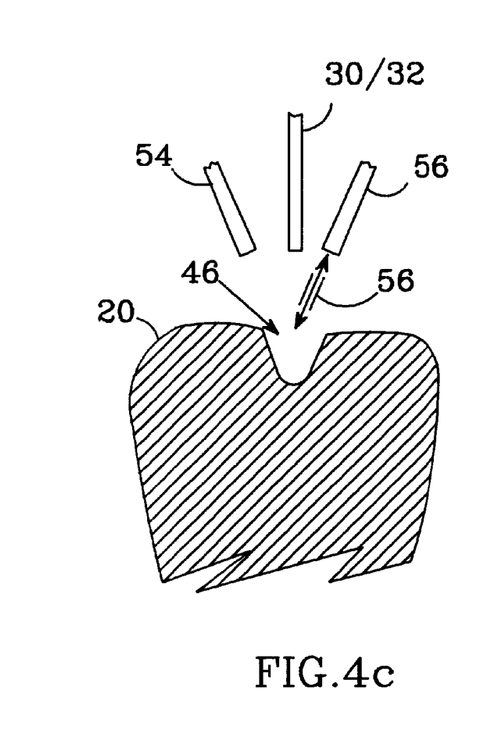

The cleaning ability of fluid 52 can be enhanced by addition of a surfactant, sequestering agent or detergent, such as sodium lauryl sulfate, phosphates or polysorbates. This addition improves the debris removal process, by the beneficial effects of the detergents, resulting in higher repetition rates. The above process is repeated until ablation of target 20 has been effected (step 316). In the event that fluid jet 54 is incapable of fully removing residual fluid or debris 50 from ablation area 46 a gaseous fluid or vacuum 56 can be used, see FIG. 4(c). The gaseous fluid or vacuum is produced by source 28 and can also be used for drying target 20, if necessary.

Figure 5:
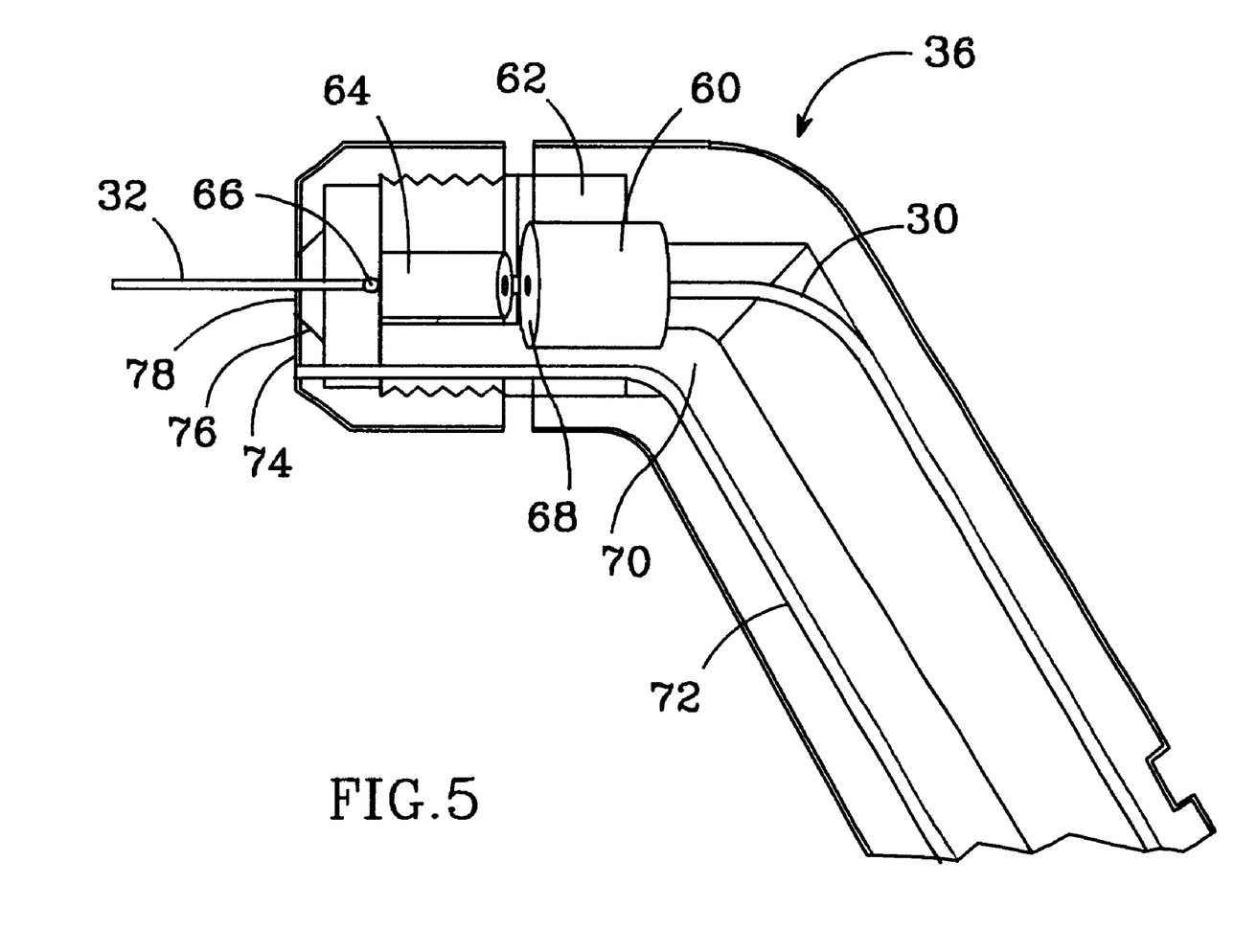
FIG. 5 is a sectional view of a laser/liquid delivery system incorporated in the invention.

FIG. 5 is a cross-sectional view of a delivery system 24 utilized by the present invention. At the outset, it is noted that while a single fiber "feed-through" system can be used to couple the laser light to target 20, if the tip or end portion of fiber 30 adjacent to target 20 is damaged or contaminated, the entire fiber 30 must be replaced. This requires removing fiber 30 from handpiece 36 and decoupling it from laser 22. Accordingly, such feed-through fiber systems can be disadvantageous. As such, a two fibers system used to supply light to the target 20 would be preferred.

As shown in FIG. 5, fiber 30 with its associated protective cabling is fitted within ferrule 60, which is inserted into one end of fiber-to-fiber coupler 62. The other end of fiber-to-fiber coupler 62 receives a ferrule 64 having fiber 32 fixed therein, thereby forming the disposable fiber optic tip discussed above. Preferably, ferrule 64 includes a capillary tube 66 formed of a laser-tolerant material (Pyrex, silica or sapphire depending on the wavelength being used) surrounding fiber 32. Capillary tube 66 permits fiber 32 to have a smaller diameter because any energy that is not transmitted by fiber 32 (due to scattering or refraction) is absorbed by capillary tube 66. Since capillary tube 66 is more laser-tolerant than metal, a common ferrule material, damage to ferrule 64 is avoided. Moreover, capillary tube 66 can have a tapered portion near the output tip of fiber 32, in order to allow laser energy to leak out in a moderate fashion directed away from the tip.

Preferably, ferrule 64 is positioned sufficiently close to ferrule 60 so that substantially all laser light emitted by optical fiber 30 is received by optical fiber 32. This can be achieved by spacing ferrules 60 and 64 from each other by a gap 68 of approximately 25 microns to 100 microns. Accordingly, with this configuration, lenses or other focusing optics are not required in order to couple light between the two fibers.

As further shown in FIG. 5, fracturing fluid and gas/vacuum lines 70 and 72, respectively, are housed within handpiece 36 carrying the corresponding fluids. These lines are preferably thin stainless steel tubes connected to their corresponding lines 44 and 42 within sheath 34. Cap 74 preferably includes a cavity 76 for directing fracturing fluid 52 through orifice 78 surrounding optical fiber 32. Cavity 76 also determines the resulting shape of the output spray of fracturing fluid 52 from handpiece 36. In this embodiment, fracturing fluid 52 cover fiber 32 removing debris adhered to the tip and interacts with ablation zone 46 to further ablating target 20 and removing corresponding debris.

Figure 6:
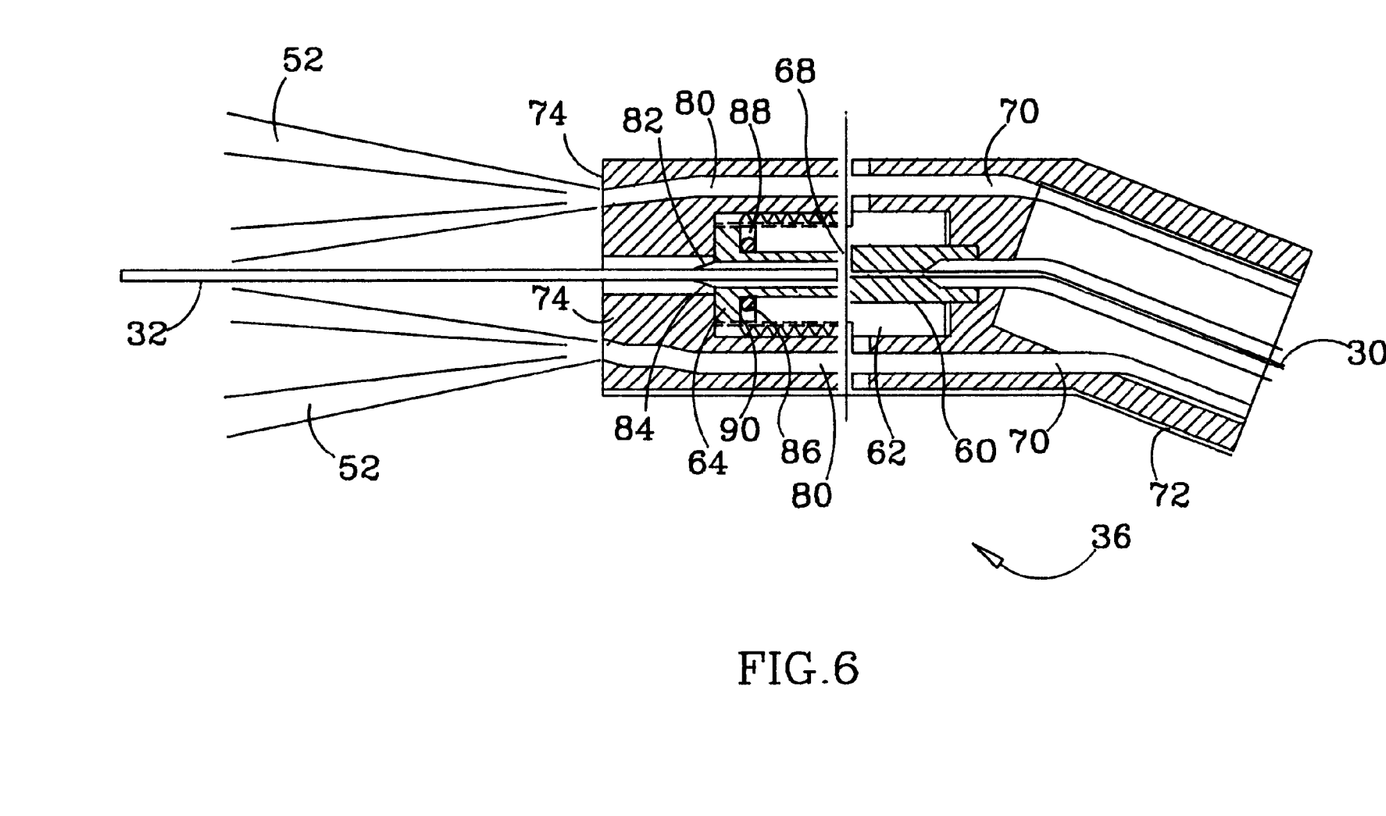
FIG. 6 is a sectional view of an alternate delivery system.

FIG. 6 illustrates an alternative delivery system 24 utilized by the present invention. As shown in FIG. 6, ferrule 64 is mounted within a cap 74 having openings 80 bored therein. Openings 80 are preferably aligned with tubes 70 to supply fracturing fluid 52 to target 20. Fracturing fluid 52 cover fiber 32 removing debris adhered to the tip and interacts with ablation zone 46 to further ablating target 20 and removing corresponding debris. Gas/vacuum line 72 is housed within handpiece 36 supplying the respective fluid.

As further shown in FIG. 6 fiber 30 and its associated protective cabling are fitted within ferrule 60. Preferably, fiber 30 extends beyond its protective cabling by a length of approximately 4 to 7 times its diameter in order to insure that fiber 30 is properly secured to ferrule 60, which is inserted into one end of fiber-to-fiber coupler 62. The other end of fiber-to-fiber coupler 62 receives ferrule 64 having fiber 32 fixed therein. Preferably, ferrule 64 includes a sleeve 82 (similar to capillary 66 discussed above) formed of a laser-tolerant material (Pyrex, silica or sapphire depending on the wavelength being used) surrounding fiber 32. Dielectric sleeve 82 permits fiber 32 to have a smaller diameter because any energy that is not transmitted by fiber 32 (due to scattering or refraction) is absorbed by sleeve 82. Since sleeve 82 is more laser-tolerant than the ferrule metal, damage to the ferrule 64 is avoided, and the fiber 32 is protected. Moreover, sleeve 82 has a tapered portion 84 in order to allow laser energy to leak out in a moderate fashion.

As further shown in FIG. 6, an O-ring 86 is fitted around a reduced diameter portion of ferrule 64 to impose a compression gap 88 between face 90 of ferrule 64 and fiber-to-fiber coupler 62. Moreover, ferrule 64 fits snugly into fiber-to-fiber coupler 62 so that a sufficiently small gap 68 is maintained between fiber 30 and fiber 32. Accordingly, substantially lossless transmission of light can occur between these two fibers without lenses or other focusing optics.

Figure 7:
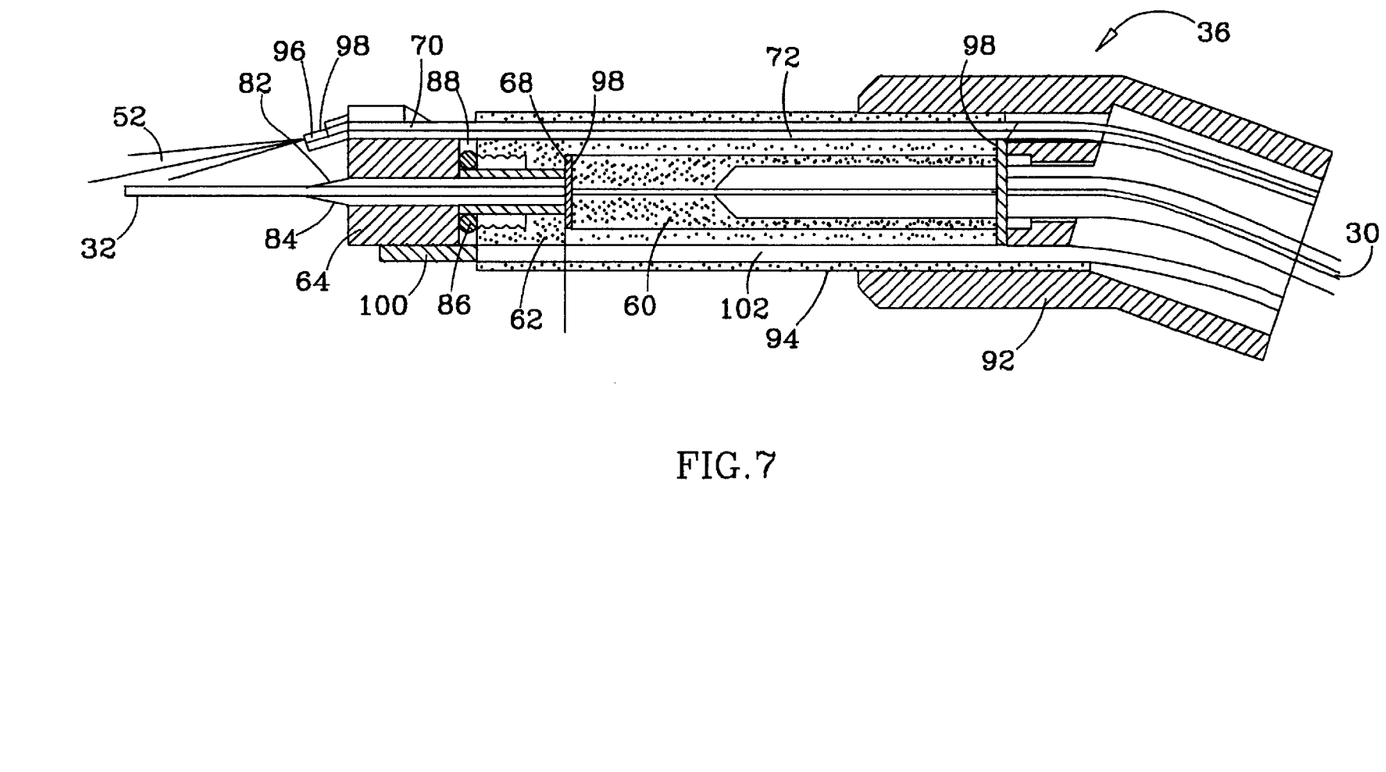
FIG. 7 is a sectional view of a third delivery system.
Figure 8A:
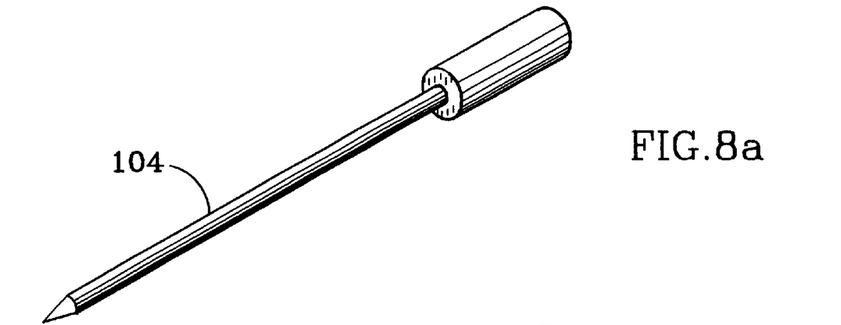
FIGS. 8(a)–8(d) are perspective views of disposable fiber tips of varying designs that can be used with the invention.
Figure 8B:
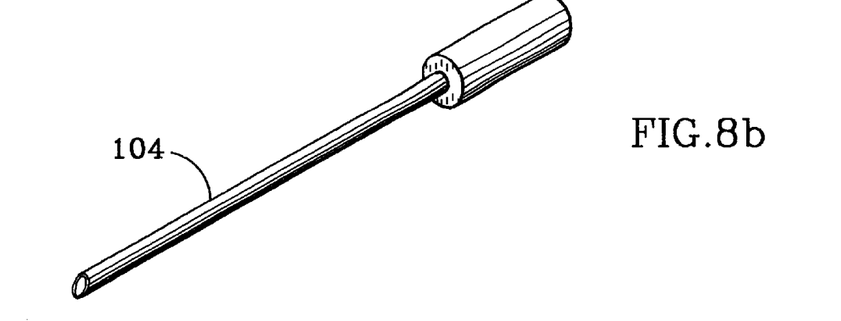
Figure 8C:
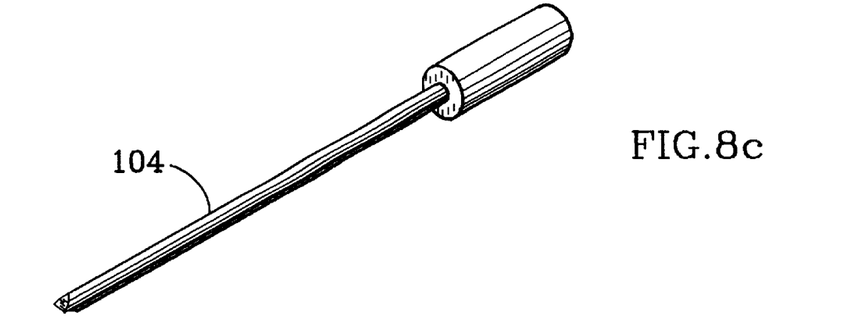
Figure 8D:
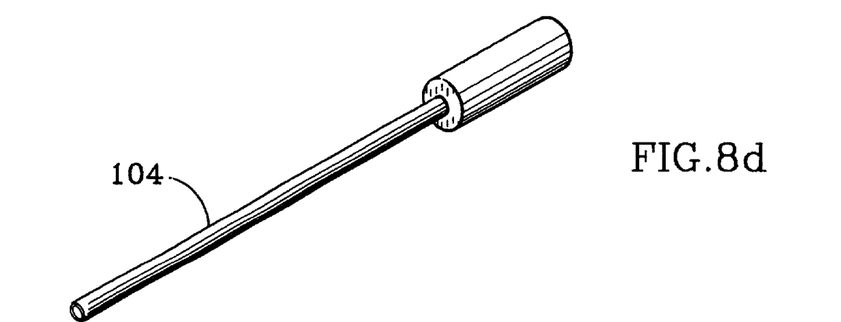

FIG. 7 illustrates another alternative delivery system 24 utilized by the present invention. Handpiece 36, shown in FIG. 7, is similar to that discussed above however, it includes a two-piece outer casing including a first portions 92 and a second portion 94. Moreover, fluid jet 54 is provided within housing 96 at the discharge end portion of fracturing fluid line 70. With this construction, a focused fracturing fluid spray 52 can be generated. In addition to facilitating ablation of ablation site 46, as discussed above, fluid jet 54 also can be used, depending on its orientation and spray pattern, to remove debris blown back onto the face of fiber 32. Also provided within housing 96 is gaseous fluid/air jet which in turn is connected to line 70.

As further shown in FIG. 7, precision bearing devices 98 are provided within handpiece 36. These bearing devices allow ferrule 60 to rotate relative to the housing of handpiece 36. Thus, torque experienced by fiber 30 is reduced.

In addition, an acoustic sensor 100 is preferably coupled to ferrule 64 to convert sonic energy (i.e., noise or shock) emanating from the target area into electrical signals. As this sonic energy is believed to be an indication of the amount of material ablated or removed from the target, these electrical signals can be used to control the output of laser 22. In particular, the electrical signals are preferably conducted by wiring 102 running through handpiece 36 to laser 22.

It will be apparent to those skilled in the art that various modifications and variations can be made in the use of the laser cutting device in accordance with the present invention and in the construction of this laser cutting device without departing from the scope or spirit of the invention. Although FIGS. 5–7 illustrate a dual fiber configurations, several other method could be used, including but not limited to, a single feed through fiber 30, a series of one or more optical device, or any combination thereof which is capable of providing laser light to target 20. If a series of optics is chosen to deliver the laser light to target 20, the optics should be selected and optimized such that debris 50 is removed from ablation cite 46 with the least interference with laser beam.

As noted above, preferably fiber 32 and ferrule 64 are formed as a disposable tip 104 detachable from handpiece 36 to allow for cleaning of the fiber interface with a gas purge (air, nitrogen, or argon gas) to remove all water content from the fiber interfaces in the gap between fibers 32 and 30, thereby preventing thermal destruction and light attenuation at the fiber interfaces. Moreover, impurities in the water can absorb light in the 2–19 micron spectral range, and it is therefore important that they be removed as well in order to insure optimum operation.

Preferably, fiber 32 of tip 104 is made from single crystal sapphire, and can be easily replaced if damaged or contaminated by easily removing tip 104 from handpiece 36. Further, tip 104 can be removed prior to autoclaving or sterilizing the handpiece, thereby preventing damage to fiber 32. Any fiber other than sapphire that can transmit these mid infrared wavelengths (2.2–19 microns spectra) can not be autoclaved because they are usually hygroscopic and/or heat sensitive. Further, the combination of two fibers (32 and 30) is advantageous because it obviates the need to replace fiber 30 whenever the output end or tip becomes contaminated or damaged. Moreover, lenses or other focusing optics are not required.

FIGS. 8(a)–8(d) show four geometries of tip 104: cone, 1-sided chisel, 2-sided chisel, and blunt, respectively. Other geometries are also contemplated, included but not limited to, ball ends and triads. If fiber optics, such as fiber 30 or 32, are used to deliver laser energy to target 20, the fiber must be located very close to the tissue surface, approximately 1–2 mm. As a result, debris 50 is often directed back adhering to tip 104 or bouncing off back into crater 48. In both cases, debris 50 continues to absorb laser energy, thereby impeding ablation efficiency. A tapered tip design, such as a cone or a chisel, will not only direct the laser light to target 20 but shall also reduce or eliminate contamination of tip 104 by debris 50. Contaminations of tip 104 can further be reduced or eliminated by subjecting it to direct or indirect interaction with fracturing fluid 26. Thus, fracturing fluid 26 will act as cleansing material to remove adhered debris. In all cases, the tip design should be optimized taking these issues into consideration. The length of the fiber 32 is preferably 10–30 mm.

Figures 9A, 9B:
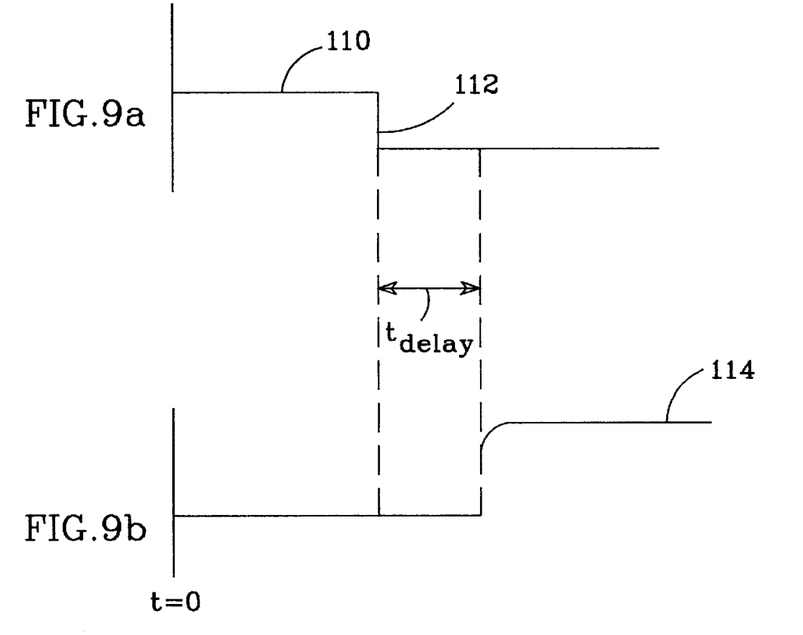
FIGS. 9a and 9b are timing diagrams of the preferred relationship between the laser pulse and the cooling fluid application in the method of the invention.

A typical timing relationship between the laser pulse and the application of cooling fluid is shown in FIGS. 9a and 9b. The laser pulse 110 is shown in FIG. 9a, with falling edge (turn off) at 112. A pulse of cooling fluid 114 is applied to the target material preferably immediately after the falling edge 112 of laser pulse 110. Only a portion of the cycle is shown, in order to expand the time scale. Thus, the rising edge of the laser pulse is not shown, having occurred before t=0. In general, a very small delay time $t_{delay}$ may be present between the falling edge 112 and the fluid application 114, but it is extremely preferable that the time $t_{delay}$ be short.

The reason for application of the cooling fluid be applied within a very short time frame after terminating the laser pulse can be demonstrated by considering a simplified model of the target's temperature. For example, a simplified, one dimensional model predicts that the target temperature in the heated region will begin rapid cooling immediately upon removal of the heat source (laser radiation). If we assume negligible heat diffusion during the laser pulse, after the pulse ends an exponential temperature gradient will be present in the target material, approximately as represented in FIG. x1. Although x is a one dimensional parameter most clearly associated with depth into the target material, similar gradients will exist in the directions perpendicular to x within the region outside the laser spot.

The temperature distribution as a function of depth into the material x (or the equivalent directions away from the laser spot) will approximate an exponential function defined by:

$$\Delta T(x) = \frac{\varepsilon_o k}{\rho C_p} e^{-kx}$$

where T(x) is the temperature as a function of x, $\varepsilon$ is the energy fluence of the pulse, k is the absorption coefficient of the target material, ρ is the density of the target material, and $C_p$ is the heat capacity of the target material.

Figure 10:
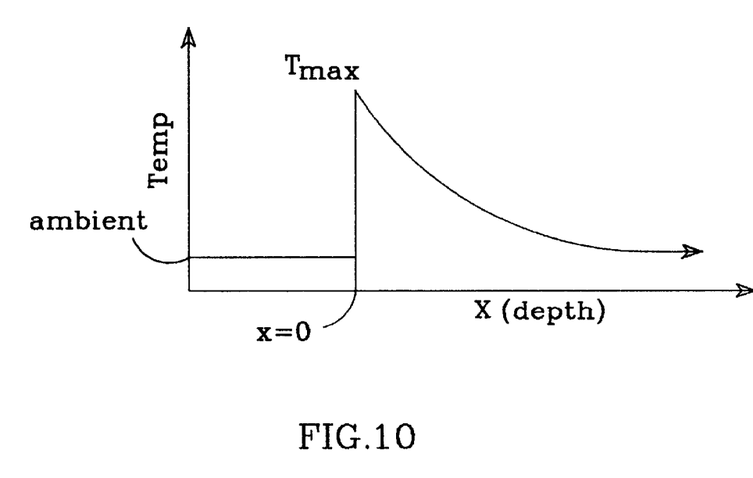
FIG. 10 is a graph of Temperature vs. depth into the target at the precise time that the laser radiation is switched off, for an exemplary material.
Figure 11A:
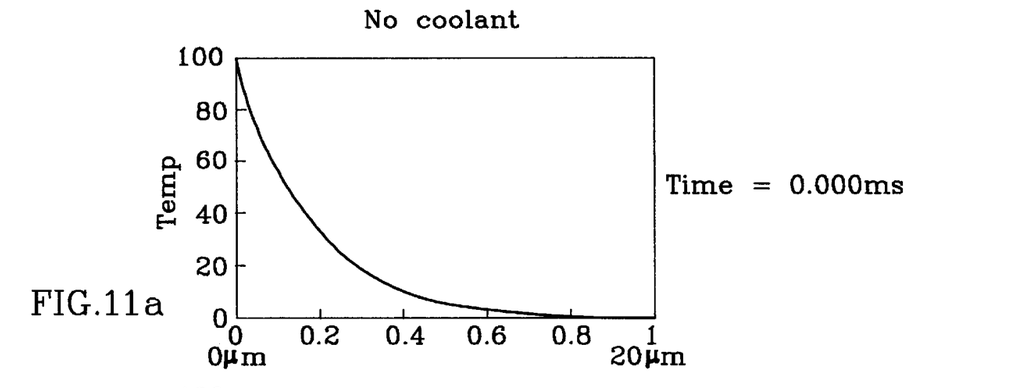
FIGS. 11a through 11d are a time sequence of graphs of Temperature vs. depth into the target at respective times 0.000 ms, 0.01 ms, 0.05 ms, and 0.10 ms after the termination of the laser pulse, for an exemplary target material without application of cooling fluid.
Figure 11B:
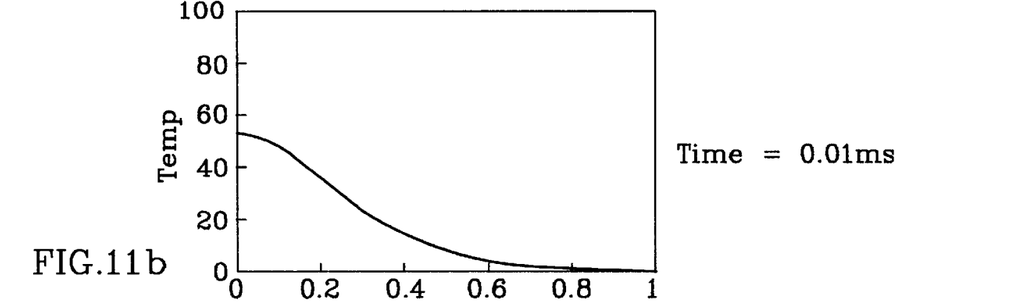
Figure 11C:
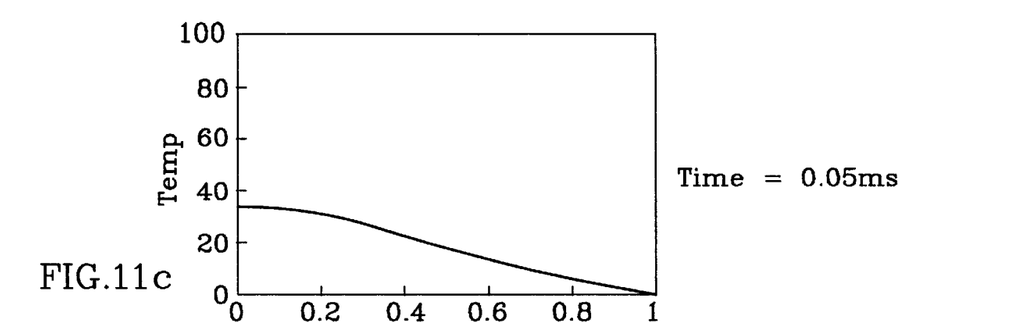
Figure 11D:
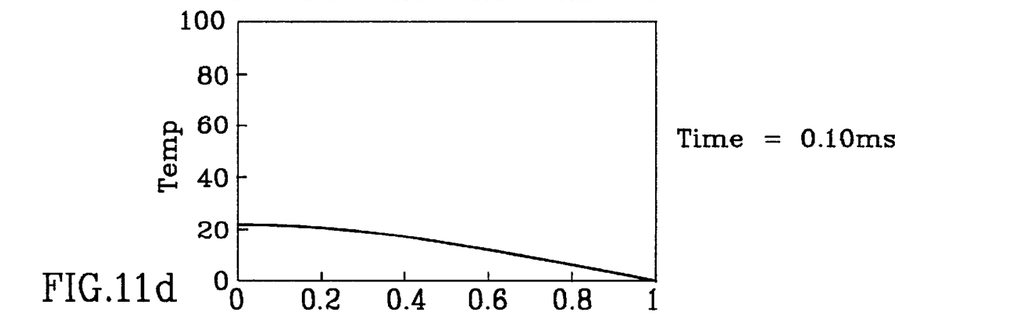

FIG. 10 merely depicts the temperature distribution at a static time, arbitrarily set to t=0 at the falling edge of the laser pulse. After the heat source (laser spot) terminates, the thermal conditions will evolve according to well known differential equations. To appreciate the approximate behavior, we consider the one dimensional case (thermal transport along a thin, narrow bar). In such a case the transient, time varying thermal behavior is governed by the equation:

$$\alpha^2 \frac{\partial^2 T}{\partial x^2} = \frac{\partial T}{\partial t}$$

where $\alpha^2$ is a constant known as diffusivity and given by:

$$\alpha^2 = \frac{k}{\rho C_p}$$

where ρ is the target material's density in grams/cm$^3$, k is the thermal conductivity of the material in watts/cm-degree C, $C_p$ is the heat capacitance in J/g-degree C.

Table 1 gives some typical materials' parameters for dental and bone-like materials. It should be understood that the values given are approximate.

TABLE 1

|  | Enamel wet | Dent in wet | Enamel dry | Dent in dry |
|---|---|---|---|---|
| ρ(@ 25° C.) | 2.84 | 2.11 | 2.72 | 1.86 |
| K | .0200 | .009 | .0172 | .01 |
| $C_p$(solid) | .72 | 1.13 | .72 | 1.13 |
| $C_p$(dry) | .72 | 1.13 | .56 | .73 |
| % $H_2O$ | .146 | .279 | .302 | .0380 |

Both dry and wet values are given because it has been found that the dry values, which differ in general from those of the wet materials, are more accurate in the context of the ablation method of the invention (perhaps because the tissue dries rapidly during laser heating).

FIGS. 11a through 11d, above, show a typical time evolution sequence of the temperature distribution within a typical hard tissue, assuming the values:

$\alpha^2$=5×10$^{-3}$ cm$^2$/s

K=2793 cm$^{-1}$

ρ=2.84 g/cm$^3$ $\varepsilon_o$=50 J/cm $C_p$=72 J/g° C.

Figure 12A:
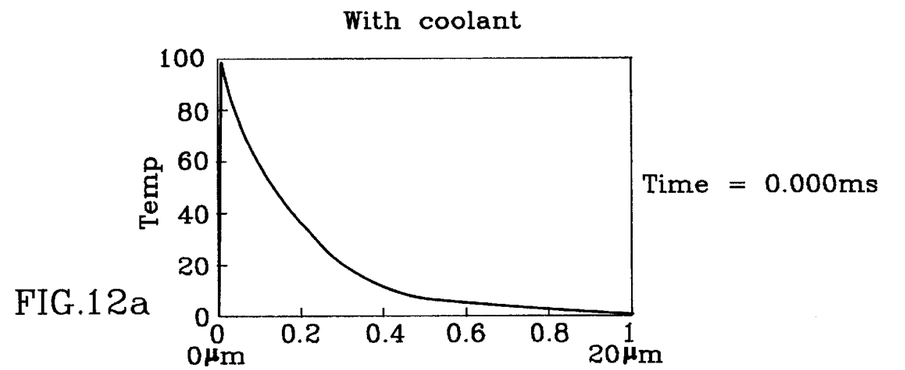
FIGS. 12a through 12d are a time sequence of graphs of Temperature vs. depth into the target at respective times 0.000 ms, 0.01 ms, 0.05 ms, and 0.10 ms after the termination of the laser pulse, for an exemplary target material with immediate application of coolant upon termination of the laser pulse.
Figure 12B:
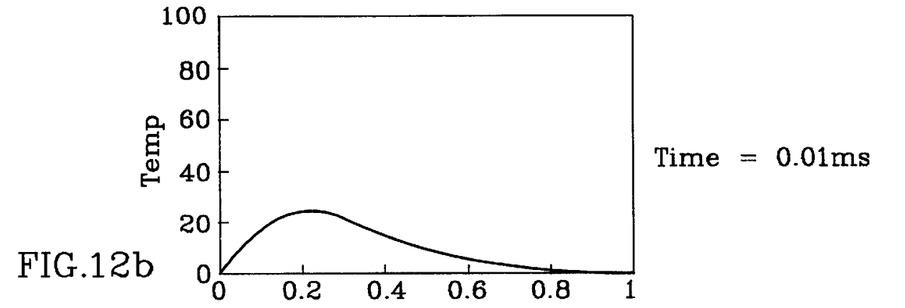
Figure 12C:
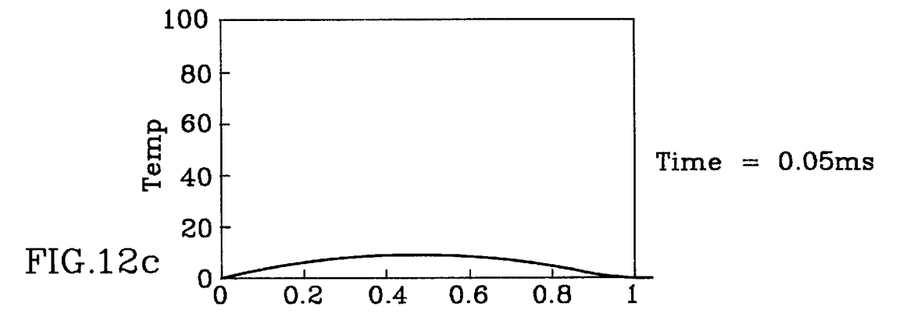
Figure 12D:
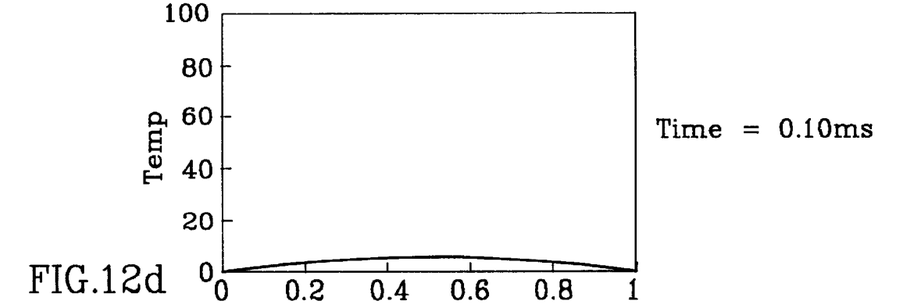

FIGS. 11a–11d represent the situation where no coolant is applied. A different situation with application of coolant is shown, for the same assumed material, in FIGS. 12a–12d. The figures assume that the coolant is applied at t=0.000 milliseconds. FIG. 12b shows with particular clarity that a thermal pulse is created, with large thermal gradient on both the rising and falling edges. To most effectively ablate the material, the thermal gradients on both sides (heating and cooling) should preferably be large enough to cause failure of the material, leading to ablation.

From the above discussion it is apparent that the temperature begins to decline immediately after the removal of the heat source (laser) as might be expected, and decreases in an approximately exponential fashion with time constant $t_r$. That is to say, that the temperature at the target's surface and near laser spot center will decrease by a factor of 1/e every $t_r$ seconds. In order to produce ablation by cooling, the coolant must be applied soon enough that a large temperature gradient can be produced, sufficient to cause thermal failure. This can only occur if the coolant is applied within a comparatively few time constants after turning off the laser heat source, and preferably should be applied immediately after the laser pulse ends.

The time constant $t_r$ is manifestly a function of the particular materials which compose the target. The invention is particularly well suited to ablate hard biological tissues such as bone or dental tissues (tooth enamel and dentin). Such tissues typically have relatively high thermal conductivity (as compared to softer materials). Thus, the time constants $t_r$ associated with such materials are typically short. For example, consider a material with $\alpha^2$ equal to $5 \times 10^3$ cm$^2$/s (in the middle of the range of values from table 1). The relaxation time can be approximated by calculating the time for the root mean squared heat displacement to equal the absorption depth for a typical pulse, according to the relations:

$$1/k = \text{absorption depth} = \sqrt{2a^2 t_r}$$

solving for $t_r$, assuming k=2793 cm$^{-1}$, we obtain a $t_r$=13 microseconds (approximately).

The actual relaxation times of biological materials will, of course, vary according to the material properties, and may in general not be constant for all temperatures. Nevertheless, in most materials and practical conditions, the coolant should be applied as soon as possible after the falling edge of the heating pulse, and in no event later than one millisecond after the falling edge of the laser pulse. It is preferable that the coolant be applied within a $t_{delay}$ of 100 microseconds; most preferably the coolant should be applied immediately (less than 10 microsecond $t_{delay}$).

In terms of relaxation time constants $t_r$ (which will vary by material) it is preferable that the coolant pulse be applied within n time constants (after the falling edge of the laser pulse) where n is less than 10.

It should also be understood that the relaxation times are somewhat dependent on the spatial dimensions of the laser spot (on the target material). Table 2 gives typical beam parameters which have been found useful for accurate and fast ablation.

TABLE 2

| | |
|---|---|
| Wavelength | 2.94 × 10$^{-6}$M |
| Beam Radius | 5.64 millimeters |
| Pulse Width | 8.30 × 10$^{-5}$ seconds |
| Rep. Rate | 5 to 100 Hz |

The short relaxation times for typical hard biological tissue has significance for the invention. The shorter the time lag before application, the better the ablation which should result. However, continuous fluid application (or application which commences during the laser pulse) is somewhat undesirable because the coolant tends to absorb radiation and/or heat during the laser pulse, reducing heating efficiency of the laser and cooling efficiency of the fluid. Therefore, it is preferable to alternately apply the laser radiation and cooling fluid in pulses, with less than 1 millisecond time lag between the end of the laser pulse and the beginning of the fluid application (to the target surface). For best results, it is most preferred that the time lag be even shorter, for example in the microsecond range. It is most effective if the surface of the target material is substantially free of fluid before applying the laser radiation, for best absorption.

The short time lags required can be achieved by tuning the fluid delivery system so that the fluid pulse arrives at the appropriate time. Fast pulses of fluid can be obtained by various conventional means. For example, a high speed valve or rotor can be used to chop a high speed jet, or small piezoelectric diaphragm pumps could be used. Preferably the fluid pulse should be generated by a method that provides a sharp leading edge. The time of arrival at the target adjustable by various means, including adjusting the distance to the target, the phase of the pulse, or the velocity of the fluid.

To achieve a high thermal gradient and thereby promote ablation, the fracturing fluid should preferably be applied directly to the same region of the target which was laser irradiated. To ensure that this occurs, the material should preferably remain substantially stationary with respect to the fluid dispenser between the application of said laser radiation and the application of the fracturing fluid. Equivalently, the dispenser should remain substantially stationary with respect to the target during the same interval. More specifically, the target should not be displaced with respect to the dispenser by more than approximately one laser spot diameter between application of the laser light and the application of the cooling fluid. This insures that strong local, time varying temperature gradients are produced, accurately ablating at the laser spot. Note that a rapidly time varying thermal gradient is produced in every direction (depth and radially outward) from the heated laser spot.

It is theorized that a dominant mechanism for the ablation by the invention is the generation of a very nonlinear thermal distribution in the target material, and thus a very nonlinear density gradient which essentially causes the upper layer of the target material to burst or fracture. As the above calculations show, a reasonable mechanism is the generation of a time-dependent thermal pulse inside the material, which results in a region of low temperature on the surface overlying a region of high temperature below. The differences in temperature lead to differences in density, with the lower density material underneath expanding and the higher density material on top contracting. This cause fracture between the two layer.

The method described offers at least two clear advantages: First, the ablation is precisely controlled (localized) because the density gradient which causes fracture is localized near the surface of the target material. Second, little total heat is coupled into the target, since much of what is added by the laser is then removed by the cooling fluid applied to the surface.

Note that the method described above gives results somewhat dependent on the material to be ablated. Experiments indicate that the method preferentially ablates hard tissues with greater efficiency than soft tissues, which may be advantageous in medical applications. It is theorized by applicants the greater ablation efficiency in hard tissues results because the thermal properties of such tissues are quite different from those of water. To the extent that soft tissues have properties approaching those of water, it becomes difficult to create a temperature discontinuity by the application of water as convenient coolant. Soft tissues may also be more resistant to thermal failure from expansion or contraction.

While the present invention is particularly suited for dental applications, including the cutting of dentin and dental enamel, it is equally applicable to cutting other biological materials, such as soft tissue, and is well suited for orthopedic applications requiring cutting of bone and cartilage. Also, soft metals and metal alloys such as aluminum and amalgam can be mechanically ablated with the above-described laser cutting device and process.

Moreover, although an optical source of electromagnetic radiation has been described above for generating laser light, other forms of electromagnetic radiation such as microwaves may be used as well.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of ablating a material comprising the steps of:
applying alternating pulses of (a) laser radiation, and (b) a fracturing fluid to substantially the same region of a material to induce thermo-elastic failure and ablation of the material with each pulse;
removing loose material resulting from said ablation; and
repeating the above steps;
wherein the fracturing fluid is applied within a delay time $t_{delay}$ after a falling edge of said pulse of laser radiation, where $t_{delay}$ is less than the time required for the region to cool to a temperature distribution with a gradient insufficient to promote thermal failure upon further cooling by said pulse of fracturing fluid, and is less than 1 millisecond.

2. The method of claim 1, wherein said $t_{delay}$ is less than 100 microseconds.

3. The method of claim 2, wherein said $t_{delay}$ is less than 10 microseconds.

4. A method of ablating a material, comprising the steps of:
(a) applying laser radiation to a surface of said material to ablate said material through thermo-elastic failure;
(b) terminating said application of laser radiation,
(c) applying a fracturing fluid to said material after terminating said laser radiation to further ablate said material and to remove loose material;
(d) terminating said application of fracturing fluid; and
(e) repeating the above steps;
wherein said step (c) of applying a fracturing fluid is commenced within a time interval $t_{delay}$ which is shorter than one millisecond.

5. The method of claim 1, wherein said laser radiation has a wavelength between about 7 $\mu$m and about 9 $\mu$m.

6. The method of claim 1, wherein said steps are repeated at a rate of about 5 Hz to about 50 Hz.

7. The method of claim 1, wherein said fracturing fluid is not absorbent of the laser radiation and has a rapid cooling capacity and cleansing ability.

8. The method of claim 1, wherein said fracturing fluid is water.

9. The method of claim 1, wherein said fracturing fluid is a gas.

10. The method of claim 1, wherein said fracturing fluid contains a surfactant.

11. The method of claim 1, wherein said fracturing fluid is additionally applied to the device applying the laser radiation to said surface to remove contamination adhered to said device.

12. The method of claim 1, wherein said fracturing fluid is applied within 100 microseconds after terminating the the application of said laser radiation.

13. The method of claim 18, wherein said fracturing fluid is applied within 10 microseconds after terminating the application of said laser radiation.

14. The method of claim 1, wherein said laser radiation has a wavelength between about 2 $\mu$m and about 3 $\mu$m.

15. The method of claim 2, wherein said laser radiation has a wavelength of 2.94 $\mu$m.

16. The method of claim 3, wherein said laser radiation is applied to said material in pulses with pulse duration in the approximate range of 100 $\mu$s to 400 $\mu$s.

17. The method of claim 1, wherein said process of ablating said material further contains the step of reducing the amount of liquid present on a surface of said material to be ablated.

18. The method of claim 7, wherein said liquid reduction is effectuated before applying said laser radiation to said surface.

19. The method of claim 7, wherein said liquid reduction is effectuated after said fracturing fluid is applied to said material.

20. The method of claim 7, wherein said liquid reduction is effectuated by laser radiation.

21. The method of claim 7, wherein said liquid reduction is accomplished by applying a dry gas to said material surface.

22. The method of claim 7, wherein said liquid reduction is accomplished by applying a vacuum to said material surface.

23. A method of ablating a material, comprising the steps of:
providing a laser radiation system comprising:
a laser radiation source;
a radiation director for applying said laser radiation to said material to heat said material and cause it to fracture or rupture;
a fluid dispenser for applying a fracturing fluid to said material to further fracture or rupturing said material; and
a controller that alternates between said laser radiation and said fracturing fluid for application to said material;
applying laser radiation to a surface of said material to ablate said material through thermo-elastic failure;
terminating said application of laser radiation;
within one millisecond after terminating said application of laser radiation, applying a fracturing fluid to said material to further ablate said material and to remove loose material;
terminating said application of fracturing fluid; and
repeating the above steps.

24. The method of claim 23, wherein said laser radiation has a wavelength between about 2 $\mu$m and about 3 $\mu$m.

25. The method of claim 23, wherein said laser radiation is applied to said material in pulses with pulse duration in the approximate range of 100 $\mu$s to 400 $\mu$s.

26. The method of claim 23, wherein said laser radiation has a wavelength between about 7 $\mu$m and about 9 $\mu$m.

27. The method of claim 23, wherein said steps are repeated at a rate of about 5 Hz to about 50 Hz.

28. The method of claim 23, further comprising the step of reducing the amount of liquid present on a surface of said material to be ablated, prior to the application of said laser radiation.

29. The method of claim 23, wherein said fracturing fluid is not absorbent of the laser radiation, and has a rapid cooling capacity and cleansing ability.

30. The method of claim 23, wherein said fracturing fluid contains a surfactant.

31. The method of claim 23, wherein said fracturing fluid is additionally applied to the device applying the laser radiation to said surface to remove contamination adhered to said device.

32. The method of claim 23, wherein said material remains substantially stationary with respect to said fluid dispenser between the application of said laser radiation and the application of said fracturing fluid.

* * * * *